United States Patent [19]

Dentel

[11] Patent Number: 5,220,283
[45] Date of Patent: Jun. 15, 1993

[54] CALIBRATION OF STREAMING CURRENT DETECTION

[75] Inventor: Steven K. Dentel, Newark, Del.

[73] Assignee: Milton Roy Company, Arvada, Colo.

[21] Appl. No.: 713,980

[22] Filed: Jun. 11, 1991

[51] Int. Cl.[5] .......................................... G01N 27/60
[52] U.S. Cl. .................................. 324/453; 324/446; 204/402
[58] Field of Search ............... 324/438, 439, 444, 446, 324/450, 452, 453; 204/400, 402, 153.1

[56] References Cited

U.S. PATENT DOCUMENTS

| | | | |
|---|---|---|---|
| 3,368,144 | 2/1968 | Gerdes | 324/32 |
| 3,368,145 | 2/1968 | Gerdes | 324/32 |
| 3,369,984 | 2/1968 | Gerdes et al. | 204/195 |
| 3,399,133 | 8/1968 | Gerdes et al. | 210/42 |
| 3,857,088 | 12/1974 | Vesely et al. | 204/402 X |
| 3,917,451 | 11/1975 | Groves et al. | 324/71.1 X |
| 4,100,491 | 7/1978 | Newman, Jr. et al. | 324/446 |
| 4,446,435 | 5/1984 | Canzoneri | 324/453 |
| 4,449,101 | 5/1984 | Canzoneri et al. | 324/453 |
| 4,566,949 | 1/1986 | Berger | 204/402 X |
| 4,609,874 | 9/1986 | Reich | 324/438 |
| 4,704,256 | 11/1987 | Hood et al. | 422/116 |
| 4,713,618 | 12/1987 | Carlson et al. | 324/438 |
| 4,769,608 | 9/1988 | Bryant | 324/453 |
| 4,816,508 | 3/1989 | Chen | 524/300 |
| 4,825,169 | 4/1989 | Carver | 324/453 |
| 4,901,024 | 2/1990 | Miyake et al. | 324/438 |
| 4,961,147 | 10/1990 | Moore | 324/446 |
| 4,988,948 | 1/1991 | Francard | 324/444 |

OTHER PUBLICATIONS

Procedures Manual for Polymer Selection in Water Treatment Plants, by Steven K. Dentel, et al, AWWA Research Foundation, Denver (1989).
"Practical Methods for Characterizing Organic Polyelectrolytes Used in Water Treatment" by Steven K. Dentel & Beth Gucciardi, Proceedings, 1989 Annual AWWA Conference, Jun. 18–19, Los Angeles, CA.

Primary Examiner—Jack B. Harvey
Assistant Examiner—Glenn W. Brown
Attorney, Agent, or Firm—Woodcock Washburn Kurtz Mackiewicz & Norris

[57] ABSTRACT

In a streaming current detector, a standard calibration solution is used to calibrate the streaming current signal representing the charged condition in a sample fluid containing particles. The standard calibration solution is electrokinetically stable over a wide range of pH and concentration. Calibration allows direct comparison of readings from different streaming current detectors.

14 Claims, 6 Drawing Sheets

CALIBRATION OF STREAMING CURRENT DETECTION

FIELD OF THE INVENTION

This invention relates to a method of calibrating streaming current detectors, and more particularly, to an electrokinetically stable calibration solution.

GENERAL BACKGROUND

Streaming current detectors (SCD's) of the type described below are known for their inaccurate measuring of fluid samples at least for three reasons. One source of inaccuracy is that over a period of time, electrodes of a streaming current detector are covered with impurities and lose accurate readings. The second source is wear and tear of mechanical parts over a period of extended use. The third source of inaccuracy is inconsistent amplification factors. Thus, different streaming current detectors may yield inconsistent readings for the same sample fluid.

Streaming current detectors measure the charge on particles in a fluid sample stream. U.S. Pat. Nos. 3,368,144 —Gerdes, 3,368,145 —Gerdes, 3,369,984 —Gerdes et al, and 3,399,133 —Gerdes et al show streaming current detectors. U.S. Pat. No. 4,446,435 —Canzoneri and U.S. Pat. No. 4,825,169 —Carver show improvements on the streaming current detector. In the instruments shown and described in these patents, a reciprocating piston moves a sample fluid past measuring electrodes.

A direct comparison of readings from different detectors is useful. Application in parallel flow processes indeed requires such a direct comparison. Additionally, data from a streaming current detector could be directly correlated and compared to other electrokinetic data such as Zeta potential. To avoid inaccurate readings by streaming current detectors, the instruments must be calibrated on a regular basis.

In the past, some attempts were made to test the streaming current detectors by using tap water. The use of tap water as a standard solution has been directed to a determination of whether the streaming current detector fell within prescribed limits. Stated another way, the instrument was tested with tap water to make a "go/no go" determination of whether the instrument was operating properly. Tap water from the same source may be used as a standard solution for a short period of time. However, tap water from different sources has slightly different charge conditions. In fact, tap water from the same source does not have a constant charge condition over a course of time. Thus, it would be difficult to calibrate a streaming current detector with tap water.

In calibrating a streaming current detector of the above described type, it is an object of the invention to provide a simple yet accurate calibration method. This is important because it is beneficial to calibrate the streaming current detectors in the field.

Another object of the invention is to use a electrokinetically stable calibration solution with a long shelf life. Although the calibration solution may be mixed just prior to its use, it is more convenient to stockpile a solution and use it repetitively over a period of time.

A further object of the invention is that the calibration method is completed within a relatively short period of time. Time to prepare the calibration solution, clean the electrodes, and rinse with the calibration solution should be minimal to reduce the down time of the streaming current detector. For continuous measuring of fluid samples such as colloidal charge alteration control, the length of down time is critical.

Yet another object is to correlate the streaming current data to Zeta potential so that the measurement of the streaming current is confirmed.

SUMMARY OF THE INVENTION

According to the current invention, a streaming current detector of the type with a reciprocating piston and measuring electrodes for determining the charged condition in a sample fluid containing particles is calibrated with a calibration solution. The calibration method includes rinsing the electrodes with the calibration solution for a certain time while the piston is reciprocating. The calibration solution is electrokinetically stable and consistent in its charge over a wide range of pH levels. The calibration solution also easily saturates the sensor surfaces, attaining a completely charged condition. Then, a reading of the streaming current detector is taken after a predetermined time has elapsed. Lastly, the instrument is adjusted for its sensitivity according to the current reading.

In one embodiment, the calibration solution is prepared with 1,5-dimethyl-1,5-diazaundecamethylene polymethobromide. Such calibration solution has a shelf life of at least 17 days. In another embodiment, the calibration solution is prepared with polyvinyl sulfate potassium salt, and its shelf life is at least 50 days.

DETAILED DESCRIPTION OF THE PREFERRED EMBODIMENTS

Figure 1:
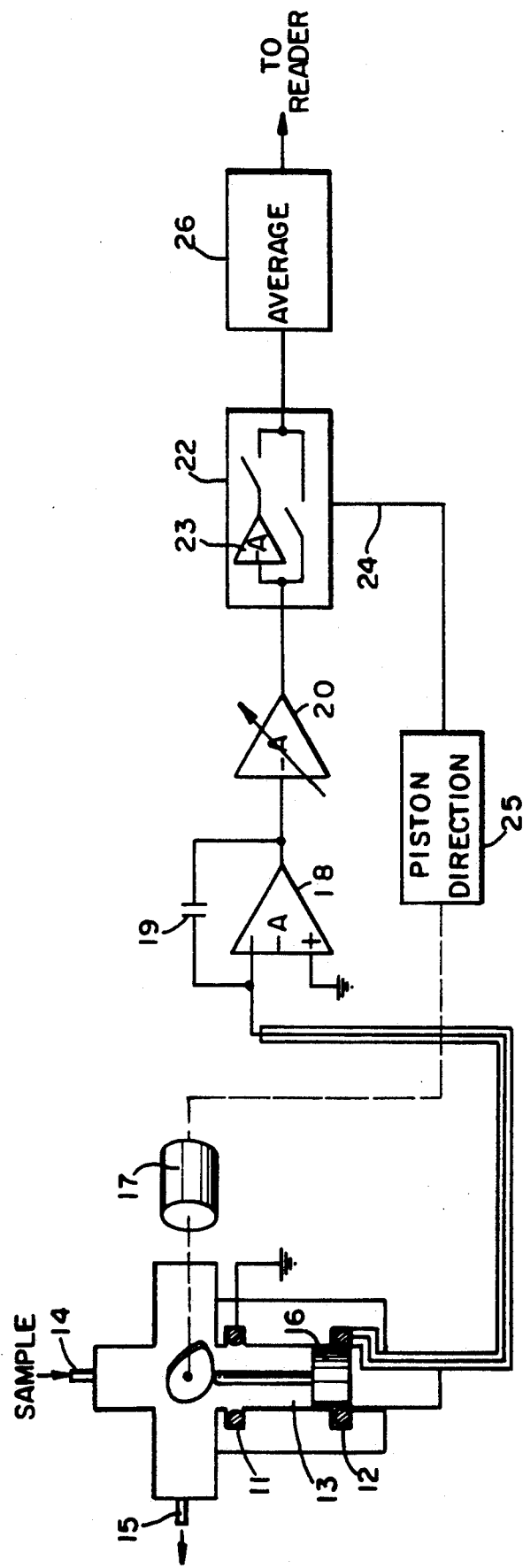
FIG. 1 shows a streaming current detector of the type to be calibrated.

FIG. 1 shows a typical streaming current detector. A pair of electrodes 11 and 12 are disposed in a bore 13. Sample fluid flows through inlet 14 and outlet 15. A piston 16 reciprocates in the bore between electrodes 11 and 12, thereby pushing sample fluid past the electrodes first in one direction and then in the other direction. A motor 17 has a shaft connected to an eccentric or the like which reciprocates the piston 16 in the bore.

electrodes 11 and 12 are connected through coaxial cable to the amplifying circuitry which includes operational amplifier 18. The output of operational amplifier 18 is further amplified in amplifier 20, the output of which is applied to the rectifier 22. Rectifier 22 is an electronic synchronous detector which includes operational amplifier 23. The output signal from amplifier 20 is directed to both the inverting and non-inverting inputs of operational amplifier 23. Electronic switches consisting of field effect transistors are appropriately connected to a control port 24 through which the selection of inverting or non-inverting amplification can be made by remote electrical signals.

The control port 24 of rectifier 22 is connected to the output of piston direction generator 25 which may typically be the light detector and light source shown in the Carver U.S. Pat. No. 4,825,169. Piston direction generator 25 generates a piston direction signal in synchronism with the reciprocation of piston 16.

The output of rectifier 22 is applied to an averaging circuit 26 which produces an output proportional to the charge of the sample fluid.

In order to calibrate the above-described streaming current detector, an electrokinetically stable calibration solution is used. To make reading very accurate, the electrodes are removed for cleaning and then installed. Clean electrodes are immersed in the standard calibration solution while the piston is reciprocating. After a stabilization period (20 minutes, for example) of running with the calibration solution, a reading is taken to adjust the sensitivity of the streaming current detector. The sensitivity is adjusted by changing the gain of amplifier 20, for example. The sensitivity is adjusted until the reading is a base streaming current signal. Thereafter, the readings from the instrument can be compared accurately with the readings of other streaming current detectors, and can be compared to other electrokinetic data.

The following criteria are used to select a calibration solution. The aqueous calibration solution containing some salt should be electrokinetically stable at various pH levels and over a broad concentration range. The salt in powder or granular form should be commercially available at low cost and readily soluble in water with minimal foaming. The salt also should have a long shelf life both in dry form and aqueous solution. Although the calibration solution should be surface active or adsorptive on the electrodes, it should be readily desorbable by water rinsing. The calibration solution should not be acidic, caustic or corrosive.

Figure 2A:
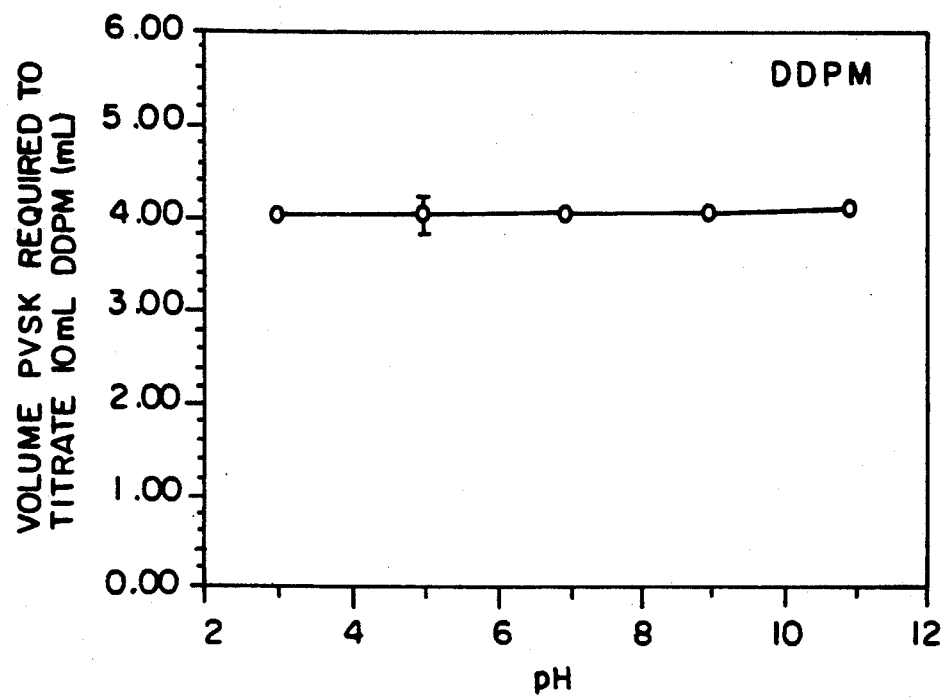
FIG. 2A shows the volume of PVSK required to titrate 10 mL DDPM to a zero net charge at different pH levels. The constant PVSK volume shows the constant charged condition of DDPM and PVSK over a wide range of pH levels.

FIG. 2A shows that both Polyvinyl Sulfate Potassium salt (PVSK, Sigma Chemical Co., St. Louis #P6000) and 1,5-dimethyl-1,5-diazaundecamethylene polymethobromide. (DDPM, Aldrich Chemical Co. Milwaukee #10,768-9) calibration solutions retain a consistent charge for a very wide range of pH levels. 0.0005N or 81 mg/L PVSK and 0.002N or 37.4 mg/L are used without adjusting pH level. Since it is known that PVSK charge condition does not change over different pH levels (Dentel, S. K. et al, *Procedures Manual for Polymer Selection in Water Treatment Plants*, AWWA Research Foundation, Denver, (1989); Dentel, S. K. and Guacciardi, B. M. "Practical Methods for Characterizing Organic Polyelectrolytes Used in Water Treatment," Proceedings, 1989 Annual Awwa Conference, Jun. 18-19, Los Angeles, Calif.), the constant PVSK volume for titrating to a zero net charge indicates constant DDPM and PVSK charge conditions at different pH levels. The electrokinetic characteristics of the calibration solution must be stable so that every time the solution is used, the same streaming current values can be expected. This characteristic in the calibration solution is crucial.

Figure 2B:
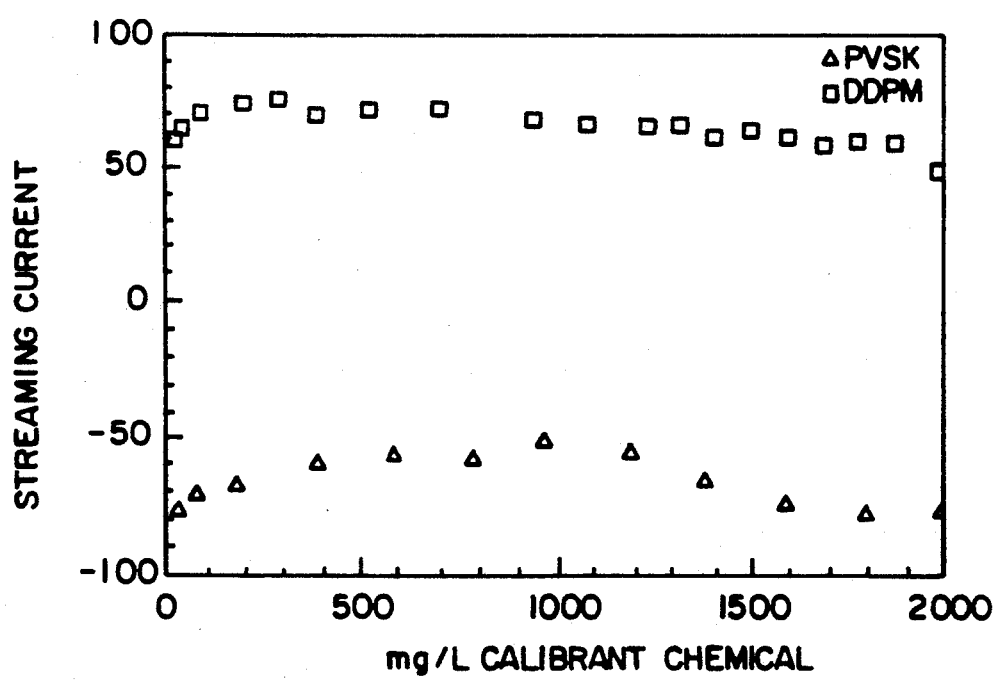
FIG. 2B shows streaming current value measured by the streaming current detector as a function of the calibration chemical concentration. The streaming current for both PVSK and DDPM substantially plateaus approximately in the 750 mg/L range, defining the standard concentration.

FIG. 2B shows the effect of concentration of the calibration solution on streaming current. Different concentrations of PVSK and DDPM were prepared at the same pH level. Streaming current was measured by a streaming current detector (Milton Roy, Model Gen II, S/N 700401) for each concentration which ranged from 25 mg/L to 2000 mg/L. Both calibration chemicals show a plateau trend in streaming current with increased concentrations. DDPM reaches a plateau in streaming current with a relatively small dose, approximately 100 mg/L, while PVSK reaches a plateau in streaming current at about 400 mg/L. 750 mg/L was chosen as the standard calibration concentration for both PVSK and DDPM since this concentration is the flattest part of the PVSK curve and the dosage that will allow for the largest variability in dose with a constant streaming current valve. For convenience, the same concentration was selected for DDPM. At this standard concentration, the streaming current value for DDPM is adjusted to $+60\pm3.8$, while that for PVSK is adjusted to $-59\pm3.5$. The units of these values are arbitrary digital units based upon actual streaming current measured by the streaming current detector.

Figure 3A:
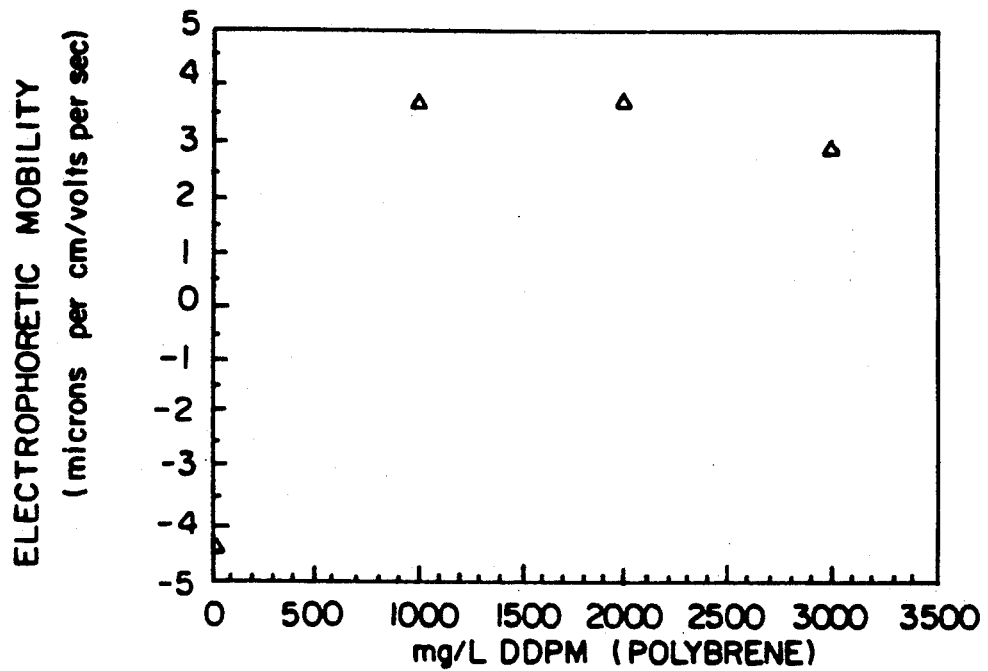
FIG. 3A shows the Zeta potential of the solution measured by a Zeta-meter as a function of concentration of DDPM which coats a negatively charged silica suspension of min-u-sil.

FIG. 3A shows an electrophoretic mobility (EM) reading of approximately $+3.5$ ($\mu$m/sec) (V/cm) by a Zeta-meter (Zeta-Meter Inc., N.Y. Electrophoresis cell, Type 2- UVA, S/N 2429) as a function of the DDPM concentration. For the experimental conditions, this is equal to a zero potential of 49 mV using a conversion factor of 14. The Zeta-meter measures the speed of the particles set in motion by the interaction between the applied electric field and the surface charge on the particles. However, since the two calibration solutions are clear and the Zeta-meter requires visibility of suspended particles, the calibration solution cannot be directly analyzed. Various concentrations of positively charged DDPM solution (0 to 3000 mg/L) are added to the negatively-charged silica suspension of 300 mg/L min-u-sil 5 (U.S. Silica, Berkeley Springs, Wyo. 25411) so that the positive charge coats the negatively charged particle surface in the suspension. The electrophoretic mobility values in FIG. 3A, and the equivalent Zeta potentials, are confirmed by the streaming current detector.

Figure 3B:
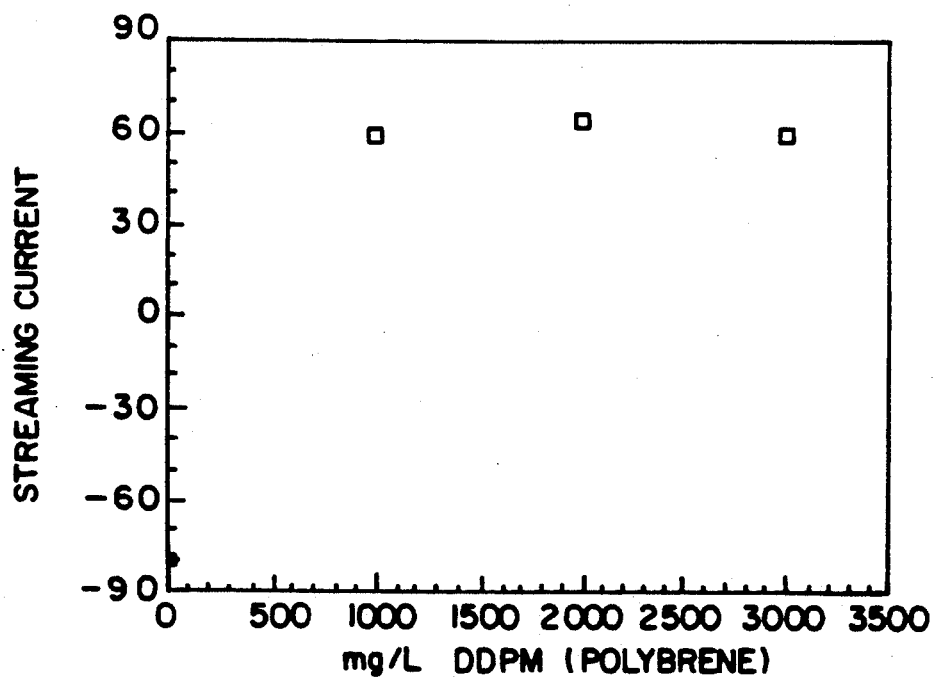
FIG. 3B shows the streaming current value measured by the streaming current detector as a function of concentration of DDPM which coats a negatively charged silica suspension of min-u-sil.

FIG. 3B shows that the same DDPM concentrations described above yield $+60$ streaming current value which is measured by a streaming current detector (Milton Roy, Model Gen II, S/N 700401) as shown in FIG. 2B indicating that the DDPM solution saturated the negatively charged particles in the suspension. Since the streaming current values using the coated particles are the same as the values with DDPM solution only, the corresponding electrophoretic mobilities are also characteristics of the DDPM. Thus, +60 streaming current value can be correlated to +3.5 ($\mu$m/sec)(V/cm) electrophoretic mobility value, and +49 mV Zeta potential.

Figure 4A:
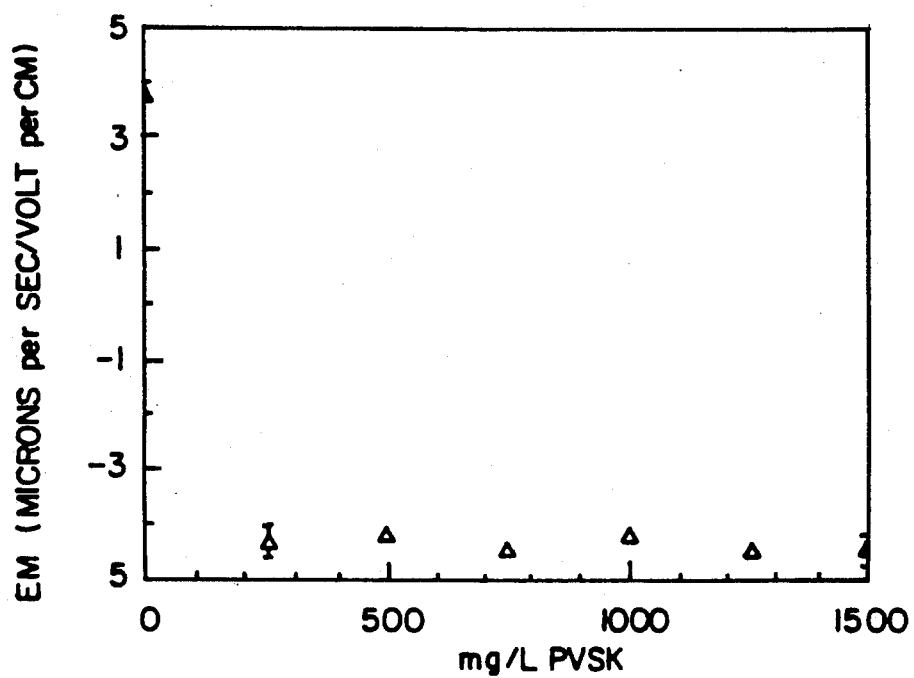
FIG. 4A shows the Zeta potential of the solution measured by a Zeta-meter as a function of concentration of PVSK which coats positively charged titanium dioxide.

FIG. 4A shows an electrophoretic mobility (EM) reading of approximately −4.2 ($\mu$m/sec)/(V/cm) by a Zeta-meter (Zeta-Meter Inc., N.Y. Electrophoresis cell, Type 2-UVA, S/N 2429) as a function of PVSK concentration. This is equal to a Zeta potential value of −59 mV. As explained with reference to FIGS. 3A and 3B, clear PVSK solution cannot be directly measured by a Zeta-meter. Thus, various concentrations of negatively charged PVSK solution (0 to 1500 mg/L) are added to coat the positively charged 300 mg/L titanium dioxide suspension (Du Pont De Nemours, Wilmington, Del. #R-107-CD). The electrophoretic mobility values in FIG. 4A, and corresponding Zeta potential, are confirmed by the streaming current detector.

Figure 4B:
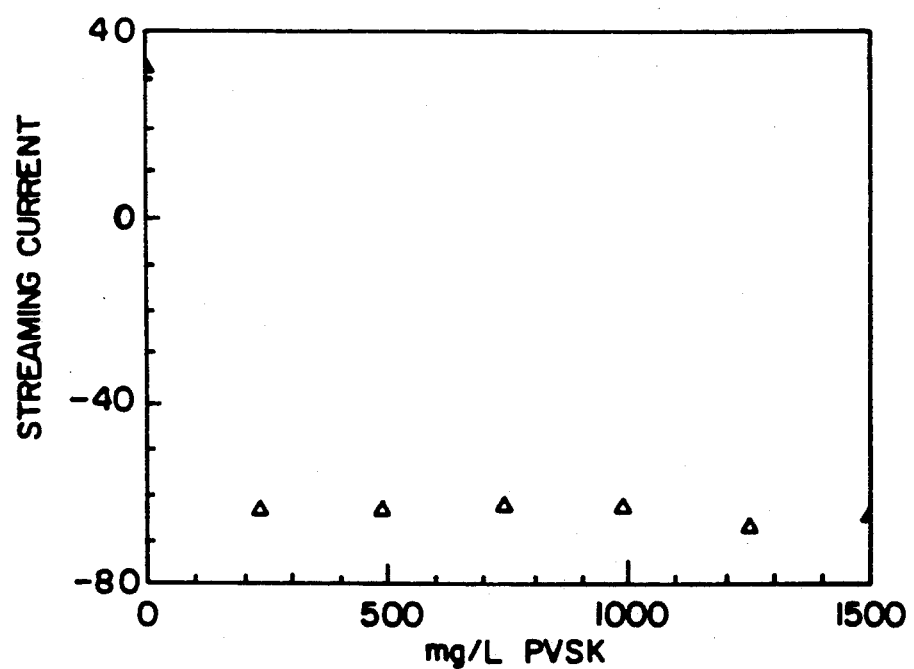
FIG. 4B shows streaming current measured by the streaming current detector as a function of concentration of PVSK which coats positively charged titanium dioxide.

FIG. 4B shows that the same PVSK concentrations described above yield −60 streaming current values which are measured by a streaming current detector (Milton Roy, Model Gen II, S/N 700401) as shown in FIG. 2B, indicating that the PVSK solution saturated the positively charged particles in the suspension. Since the streaming current values using the coated particles are the same as the values with DDPM solution only, the corresponding electrophoretic mobilities are also characteristic of the PVSK.

Figure 5:
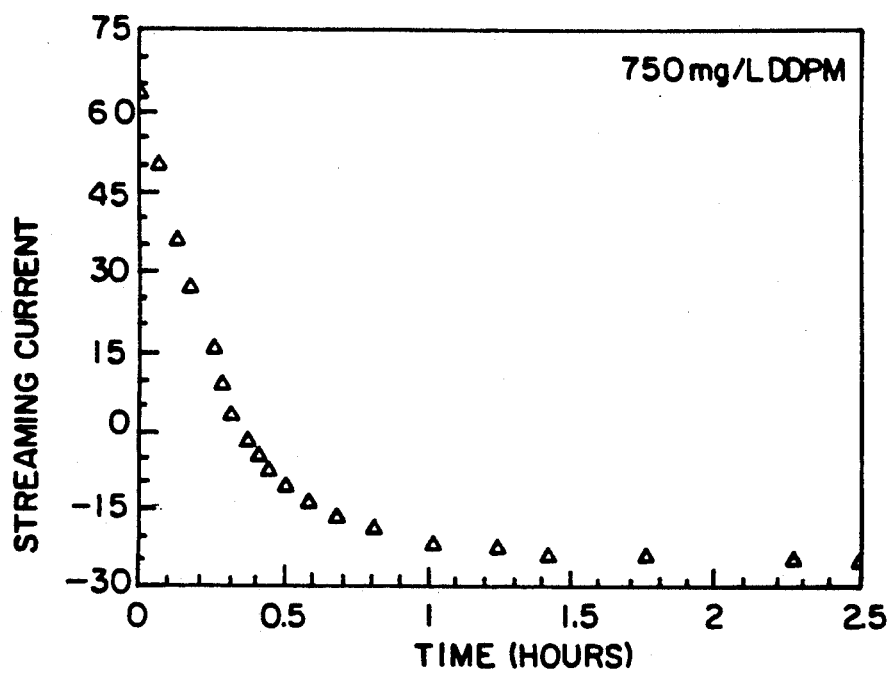
FIG. 5 shows the washability of a residual DDPM calibration solution (750 mg/L) by a constant flow of tap water (5L/minute).

FIG. 5 shows how soon the residual DDPM of the 750 mg/L standard calibration solution on a streaming current detector (Milton Roy, Model Gen II, S/N 700401) can be washed away by 5L/minute flow of tap water after calibration. The calibration solution is put in the flow-through chamber. Then, a stream of tap water is allowed to flow into the chamber to wash out the chemical, rinse the electrode and flow out the outlet. The streaming current is constantly recorded on a strip chart to determine time necessary to approach a pre-recorded tap-water streaming current value. The amount of time necessary to wash away the residual DDPM partially depends upon the flow rate. At 5L/minute, it takes one and a quarter hour as shown in FIG. 5. Although FIG. 5 does not show the washability of DDPM at different flow rates, it takes one and a half hour at 4L/minute and one and two thirds hour at 1.2L/minute respectively. Unlike DDPM, PVSK is washed away within seconds.

Figure 6:
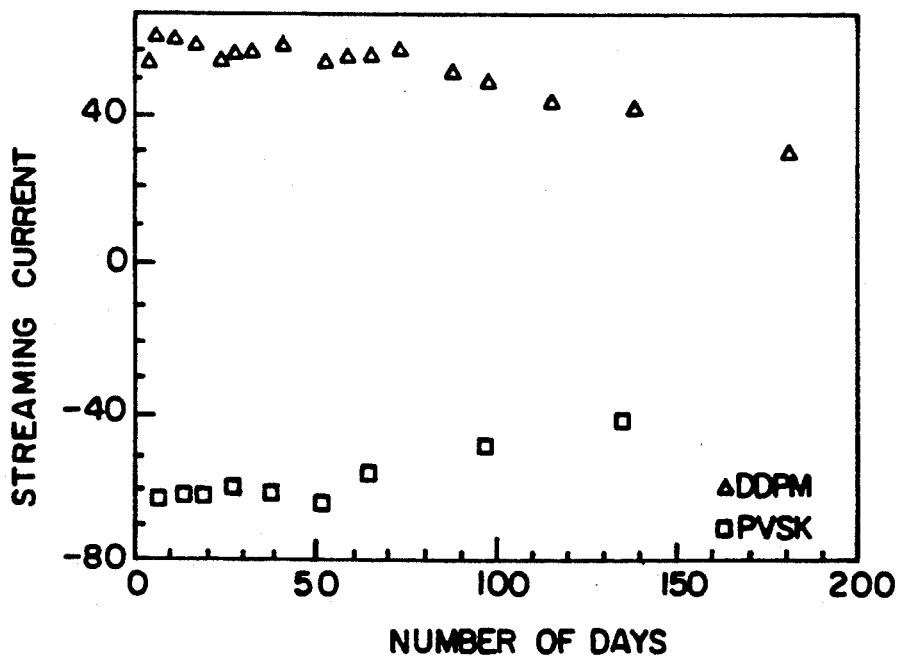
FIG. 6 shows the shelf life of the DDPM and PVSK solutions. The streaming current of each standard calibrating solution is measured by the streaming current detector and plotted against the number of elapsed days.

FIG. 6 shows shelf life of the DDPM and PVSK standard calibration solutions. The calibration solutions are stored in a beaker with a plastic film covering, and streaming current is measured by the streaming current detector (Milton Roy, Model Gen II, S/N 700401) every few days. The PVSK calibration solution retains its original streaming current value for about 50 days before it deteriorates. The DDPM calibration solution, on the other hand, retains its original streaming current value for about 70 days.

From the above-described data, the following calibration protocol is established. First, preferably fresh 750 mg/L DDPM or PVSK aqueous solution is prepared. The solution should be aged for about 24 hours to ensure thorough dissolution. Secondly, the electrode must be thoroughly washed with tap water using a test tube scrubbing brush and rinsed with distilled water. Then, the electrode is installed in the streaming current detector and rinsed with the standard calibration solution by immersing the electrode with the standard calibration solution while the piston is reciprocating for several minutes. Subsequently, the electrode should be removed from the instrument, washed and rinsed in the solution as described above two more times. This ensures that the electrode is very clean and can be well coated with the standard calibration solution. Thirdly, a reading by the streaming current detector should be taken after 20 minutes of running with the standard calibration solution. Then, without changing a multiplication factor of the streaming current detector, the variable calibration adjusting means is adjusted to make the streaming current value +60 for the DDPM standard calibration solution or −60 for the PVSK standard calibration solution. Lastly, the standard calibration solution is washed away by tap water for a predetermined time depending upon whether PVSK or DDPM before analyzing a sample fluid.

Due to an arbitrary but consistent amplification factor applied to the measured current by the device electronics, the unit of streaming current values is arbitrary. However, through FIGS. 3 and 4 they can be quantitatively converted to electrophoretic mobility values and therefore to the proportional Zeta potentials.

Figure 7:
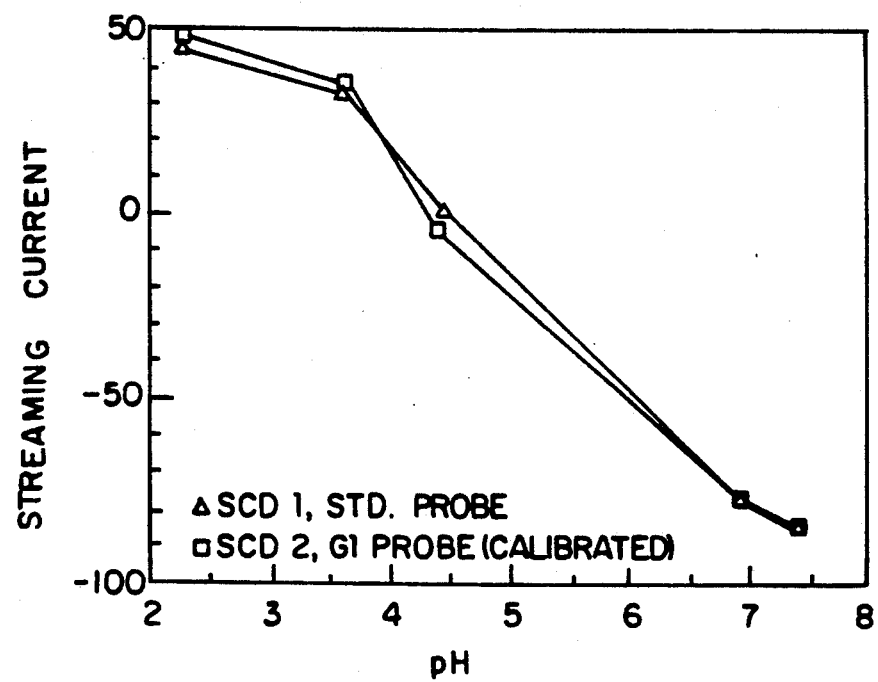
FIG. 7 shows the effect of electrode size on streaming current at different pH levels.

FIG. 7 shows the effect of electrode size on the streaming current value at different pH levels. A sample reading by Streaming Current Detector 2 (SCD2) with the non-standard electrode, G1 for which the piston-bore gap distance and resulting probe sensitivity have been altered is adjusted to confirm to the reading by SCD1 with the standard electrode by adjusting the variable calibration adjusting means. Other streaming current values by SCD2 at different pH levels are substantially correlated to those by SCD1. This demonstrates the ability to recalibrate SCD's following physical wear to the probe components. Both SCD1 and SCD2 are Milton Roy, Model Gen II, S/N 700401. However, while the piston-bore gap distance of SCD1 is 0.0125 inch, that of SCD2 is 0.0472 inch.

The advantages of the calibration method using the DDPM include its inexpensive cost and a very strong electrokinetic character. Thus, the DDPM does not require a perfectly clean electrode prior to taking a sample reading. However, it is more difficult to prepare a calibration solution because of its hygroscopic nature and to wash out the residual chemical. The PVSK has the advantage of being easily washed away after the calibration. However, the PVSK is about 6 times more expensive and requires diligent cleaning of the electrode before calibration.

While a particular embodiment of the invention has been shown and described, various other modifications are within the true spirit and scope of the invention. The appended claims are, therefore, intended to cover all such modifications.

What is claimed is:

1. A calibration method for calibrating a streaming current detector of the type having a reciprocating piston and electrodes disposed where said piston reciprocates, and variable calibration adjusting means for adjusting the sensitivity of said detector, said calibration method comprising the steps of:
    (a) rinsing said electrodes for detecting a streaming current with a standard calibration solution for a predetermined time while said piston is reciprocating, said calibration solution including a salt in said calibration solution which is electrokinetically stable and consistent in its charge over a wide range of pH, said calibration solution saturating the charged condition on the surface of said electrodes, said calibration solution producing a substantially constant streaming current signal over a range of concentrations;

(b) reading the streaming current of said solution after a predetermined time has elapsed; and (c) adjusting said variable calibration adjusting means to produce a common base streaming current signal so as to allow an accurate comparison between readings from a same or different streaming current detectors for determining a charged condition in a sample fluid containing particles.

2. The method recited in claim 1 wherein said calibration solution is prepared with 1,5-dimethyl-1,5-diazaundecamethylene polymethobromide.

3. The method recited in claim 2 wherein said reading is taken for said calibration solution of 750 mg DDPM/L.

4. The method recited in claim 2 wherein said solution has a shelf life of about 70 days.

5. The method recited in claim 1 wherein said calibration solution is prepared with polyvinyl sulfate potassium salt (PVSK).

6. The method recited in claim 5 wherein said reading is taken for said calibration solution of 750 mg PVSK/L.

7. The method recited in claim 5 wherein said solution has a shelf life of about 50 days.

8. The method recited in claim 1 wherein said electrodes are cleaned with tap water and rinsed with distilled, deionized, and filtered water prior to step (a).

9. The method recited in claim 8 wherein said cleaning and rinsing of said electrodes are repeated a predetermined number of times prior to step (b).

10. The method recited in claim 9 wherein said predetermined number is two.

11. The method recited in claim 1 wherein the predetermined time in the step (a) is several minutes.

12. The method recited in claim 1 wherein the predetermined time in the step (b) is 20 minutes.

13. The method recited in claim 1 wherein said streaming current signal is converted to equivalent units of electrophoretic mobility.

14. The method recited in claim 1 wherein said streaming current signal is converted to a Zeta potential.

* * * * *